(12) United States Patent
Hewson et al.

(10) Patent No.: US 10,791,980 B2
(45) Date of Patent: Oct. 6, 2020

(54) METHOD, DEVICE AND SYSTEM FOR ASSESING THE QUALITY OF BALANCE

(75) Inventors: David James Hewson, Torvilliers (FR); Jacques Duchene, St Andre les Vergers (FR); Hichem Snoussi, Andre les Vergers (FR); Jean-Yves Hogrel, Montrouge (FR); Yves Langeron, Villemereuil (FR)

(73) Assignee: UNIVERSITE DE TECHNOLOGIE DE TROYES, Troyes (FR)

( * ) Notice: Subject to any disclaimer, the term of this patent is extended or adjusted under 35 U.S.C. 154(b) by 997 days.

(21) Appl. No.: 13/880,493

(22) PCT Filed: Oct. 21, 2011

(86) PCT No.: PCT/FR2011/052472
§ 371 (c)(1),
(2), (4) Date: Aug. 20, 2015

(87) PCT Pub. No.: WO2012/052697
PCT Pub. Date: Apr. 26, 2012

(65) Prior Publication Data
US 2016/0007902 A1    Jan. 14, 2016

(30) Foreign Application Priority Data
Oct. 21, 2010   (FR) ..................... 10 58589

(51) Int. Cl.
*A61B 5/00*    (2006.01)
*A61B 5/103*    (2006.01)
(Continued)

(52) U.S. Cl.
CPC .......... *A61B 5/4023* (2013.01); *A61B 5/1036* (2013.01); *A61B 5/11* (2013.01);
(Continued)

(58) Field of Classification Search
None
See application file for complete search history.

(56) References Cited

U.S. PATENT DOCUMENTS

| 4,694,922 A | | 9/1987 | Mairot | |
| 5,388,591 A | * | 2/1995 | De Luca | A61B 5/1036 |
| | | | | 600/592 |

(Continued)

FOREIGN PATENT DOCUMENTS

JP    09-257556 A    10/1997

OTHER PUBLICATIONS

Translation of JP 09-257556, Japan Platform for Patent Information, www4.j-platpat.inpit.go.jp/cgi-bin/tran_web_cgi_ejje?u=http://www4.j-platpat.inpit.go.jp/eng/translation/2018031403314388422053049847 52760D2D166E141DFE36B177796AEA200102, printed out on Mar. 12, 2018, 4 pages.*

(Continued)

*Primary Examiner* — Matthew Kremer
(74) *Attorney, Agent, or Firm* — Hauptman Ham, LLP

(57) ABSTRACT

A method, device, and system for the assessment of the quality of balance and for alerting from an impairment of balance of a subject. The device comprises a plate for receiving the feet of a subject and mounted on a plurality of pressure sensors measuring vertical forces applied to the plate, wherein the method comprises the measurement, by means of the pressure sensors thereof, of vertical forces applied to the plate, at least before and while the subject mounts the device (1) and the calculation, according to the measured values, of parameters that are relevant for the assessment, including at least one parameter relating to at least one slowdown in the rise of the values measured by the pressure sensors thereof, when the subject mounts the device.

17 Claims, 6 Drawing Sheets

Figure 1:
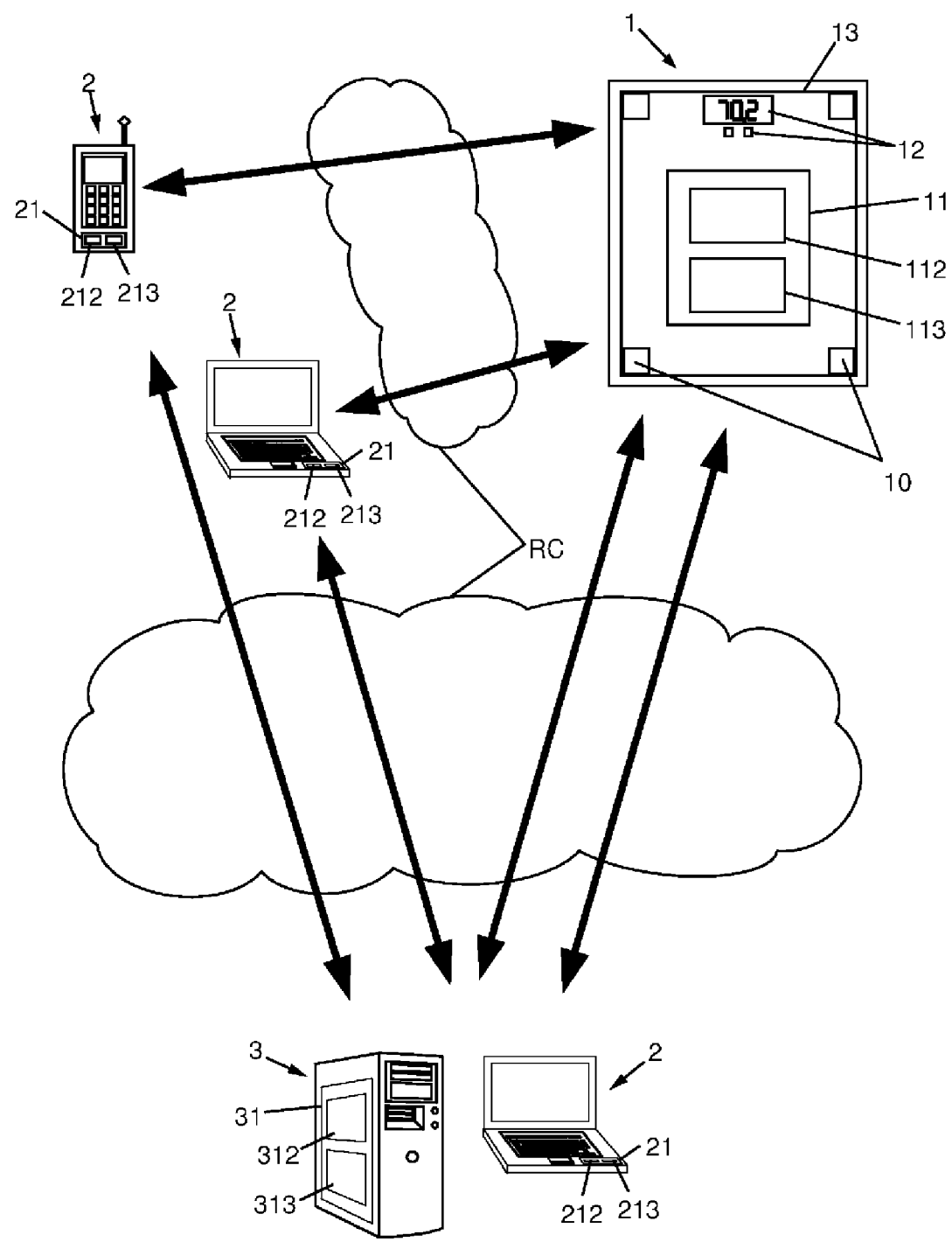

(51) Int. Cl.
  *G01G 19/44* (2006.01)
  *A61B 5/11* (2006.01)
  *G01G 23/37* (2006.01)

(52) U.S. Cl.
  CPC ............ *A61B 5/1123* (2013.01); *G01G 19/44* (2013.01); *G01G 23/3742* (2013.01)

(56) References Cited

U.S. PATENT DOCUMENTS

| | | | | |
|---|---|---|---|---|
| 5,945,610 | A * | 8/1999 | Galasso | A61B 5/1036 356/613 |
| 6,032,119 | A | 2/2000 | Jensen et al. | |
| 6,336,900 | B1 | 1/2002 | Leichner et al. | |
| 6,360,598 | B1 * | 3/2002 | Calame | A61B 5/1036 73/172 |
| 6,369,337 | B1 | 4/2002 | Machiyama et al. | |
| 2007/0250134 | A1 * | 10/2007 | Miesel | A61B 5/0488 607/45 |
| 2008/0083416 | A1 * | 4/2008 | Xia | A43B 7/142 132/200 |
| 2008/0294019 | A1 * | 11/2008 | Tran | A61B 5/0006 600/301 |
| 2009/0137933 | A1 * | 5/2009 | Lieberman | A61B 5/1036 600/595 |
| 2010/0035728 | A1 * | 2/2010 | Shinomiya | A61B 5/1038 482/8 |

OTHER PUBLICATIONS

"Elements of Sentence Construction," https://webapps.towson.edu/ows/sentelmt.aspx, Towson University, printed on Dec. 6, 2018, 10 pages. (Year: 2018).*

Michel-Pellegrino, et al., "Effect of Aging on the Weight Transfer Phase When Stepping-Down Backwards," Gait & Posture, Elsevier, vol. 24, Dec. 1, 2006, pp. S281-S282.

Jonsson, Erika, et al., "Age-related Differences in Postural Adjustments in Connection with Different Tasks Involving Weight Transfer While Standing," Science Direct, Gait & Posture, vol. 26, No. 4, Sep. 20, 2007, pp. 508-515.

Snoussi, et al., "Reconstructed Phase Spaces of Intrinsic Mode Functions. Application to Postural Stability Analysis," Conference Proceedings, Annual International Conference of the IEEE Engineering in Medicine and Biology Society, Aug. 30, 2006-Sep. 3, 2006, pp. 4584-4589.

Michel et al., 2.19 The Effect of Age on Dynamic Postural Equilibrium When Stepping Up, Gait & Posture, Amsterdam, NL, vol. 21, Jun. 1, 2005, pp. S9-S10.

Michel-Pellegrino, et al., "Evaluation of the Risk of Falling in Institution-Dwelling Elderly: Clinical Tests Versus Biomechanical Analysis of Stepping-Up," 2007 Annual International Conference of the IEEE Engineering in Medicine and Biology Society, Lyon, France, Aug. 22-26, 2007, pp. 6121-6124.

* cited by examiner

METHOD, DEVICE AND SYSTEM FOR ASSESING THE QUALITY OF BALANCE

RELATED APPLICATIONS

The present application is a National Phase application based on, and claiming priority from, International Application No. PCT/FR2011/052472, filed Oct. 21, 2011, which claims priority from French Application Number 10/58589, filed Oct. 21, 2010, the disclosure of each of which are hereby incorporated by reference herein in their entirety.

The present invention relates to the field of assessing the quality of balance. The present invention more particularly relates to a device, a system and a method for assessing the quality of balance. With the invention it is in particular possible to track the time-dependent change of this quality of balance, notably in elderly subjects, notably so as to give the possibility of preventing risks of falling by observing this time-dependent change.

The falling of persons in their daily environment is a major public health problem because of their frequency and of their medical and social consequences, notably and especially in aged subjects and in disabled adults. Intuitively, the notion of balance naturally seems to be related to the risk of falling. The relevance of this assumption has already been verified in prior studies. The relevance of the invention also relates to technological feasibility and especially socio-economic acceptability. Presently, detection of persons having a risk of falling is not very applied and not very operative, often away from daily life or humanly unacceptable.

In the prior art, laboratory systems are known such as force platforms for studying stabilograms, i.e. the study of the position of the pressure center (corresponding to the vertical projection of the center of gravity). However, these systems are sophisticated, bulky and costly. It is not possible to envision their use for patients. In fact for the time being, there does not exist any simple system which may be used at home. Therefore their exists a need for a device for assessing balance which may be routinely used for patients, at a low cost, for extracting the required information while avoiding any perturbation of usual life surroundings.

Another problem in the field relates to the methods for analyzing the assessment of balance. Indeed, various methods for analyzing balance are known, but none of them actually provides sufficiently relevant and easily measurable parameters, by means of simple and inexpensive devices. Further, the known methods are often based on relatively complex measurement procedures which generally require the assistance of a qualified operator for guiding the subject during the procedure.

Within this context, it is interesting to propose a solution for assessing the quality of balance which is based on simple and inexpensive devices, which may be easily used at home and not requiring any complex procedure.

The object of the present invention is to overcome at least some drawbacks of the prior art by proposing a method for assessing balance which is efficient and easy to apply.

This object is achieved by a method for assessing the balance of a subject, characterized in that it is applied by means of at least one device including a plate intended for receiving the feet of a subject and mounted on a plurality of pressure sensors measuring vertical forces applied on the plate, and it includes the following steps:

Measuring by means of the pressure sensors, vertical forces applied on the plate, at least before and while the subject mounts the device, Calculating, from these measured values, relevant parameters for the assessment, comprising at least one parameter relating to at least one slowdown in the rise of the values measured by the pressure sensors when the subject mounts the device.

According to another particularity, the step for calculating the parameters relating to at least one slowdown relates to at least one sigmoid and/or at least one peak in the rise of the values measured by the pressure sensors, when the subject mounts the device.

According to another particularity, the step for calculating the relevant parameters for the assessment includes a step for calculating the sum of the values measured by each of the pressure sensors.

According to another particularity, the method includes a step for broadcasting, by broadcasting means, information relating to at least one invitation of the subject to mount the device, the step for calculating the relevant parameters for the assessment including a step for calculating at least one parameter relating to the elapsed delay between the invitation to mount and the moment when the subject mounts the device.

According to another particularity, the step for calculating the relevant parameters for the assessment includes a step for calculating at least one parameter relating to the rising rate of the values measured by the pressure sensors when the subject mounts the device.

According to another particularity, the step for calculating the relevant parameters for the assessment is preceded with a step for calculating a rising phase of the values measured by the pressure sensors, when the subject mounts the device, this rising phase being determined as the period during which said values are located between 10% and 90% of a reference value reached once the subject has mounted the device, at least one portion of said calculated parameters corresponding to values calculated from this rising phase.

According to another particularity, the step for calculating the relevant parameters for the assessment is preceded with a step for calculating a so-called stability phase of the values measured by the pressure sensors, when the subject has mounted the device, this stability phase being determined as the period starting at a determined delay, a so-called waiting delay, after which said measured values have reached 90% of the reference value and ending at a determined delay, a so-called stability delay, after said waiting delay, the step for calculating the relevant parameters for the assessment comprising at least one step for calculating parameters relating to this stability phase.

According to another particularity, the step for calculating the parameters relating to the stability phase includes a step for calculating the centroid of the vertical forces measured by each of the pressure sensors in order to determine the position of the pressure center corresponding to the projection of the centre of gravity of the subject on the plate.

According to another particularity, the step for calculating the position of the pressure center over time, during the stability phase, provides a stabilogram allowing application of a modal decomposition step for extracting intrinsic modal functions therefrom, the parameters relating to the stability phase comprising at least one parameter determined on these intrinsic modal functions.

According to another particularity, the method includes at least one step for transmitting the measured values and/or the calculated parameters, through communication means of the device, towards at least one communicating terminal and/or at least one centralization server, via at least one communications network.

According to another particularity, the method includes at least one step for storing the measured values and/or the calculated parameters in memory storage means.

According to another particularity, the method includes at least one step for calculating a comparison of the measured values and/or the calculated parameters, stored in the memory storage means, for at least two determined assessments of a same subject, in order to give the possibility of tracking the time-dependent change of the quality of the balance.

Another object of the present invention is to overcome at least certain drawbacks of the prior art by proposing a device for assessing balance which is inexpensive and which may easily be installed at home.

This object is achieved by a device for assessing the balance of a subject, characterized in that it includes a plate intended for receiving the feet of a subject and mounted on a plurality of pressure sensors measuring vertical forces applied on the plate, and means for data processing laid out for applying the methods according to the invention.

According to another particularity, the plate has dimensions adapted to the average size of the feet of the subjects, so as to get rid of problems related to the position of the feet of the subjects on the plate during the measurements.

According to another particularity, the device includes display means positioned on the device so that a subject standing on the plate may see the display, so that the posture of the subjects using the device is standardized.

According to another particularity, the data processing means comprise memory storage means for applying the step for storing the measured values and/or calculated parameters.

Another object of the present invention is to overcome at least certain drawbacks of the prior art by proposing a system for assessing balance which is inexpensive and which allows centralization of the data collected at home.

This object is achieved by a system for assessing the balance of a subject characterized in that it includes at least one device according to the invention, at least one centralization server and at least one communicating terminal comprising communication means laid out for receiving the measured values and/or the parameters calculated by the device and for transmitting the received data to the centralization server.

This object is also achieved by a system for assessing the balance of a subject, characterized in that it includes a device comprising a plate intended for receiving the feet of a subject and mounted on a plurality of pressure sensors measuring vertical forces applied on the plate, and data processing means dynamically collecting the values measured by the pressure sensors at least before and while the subject mounts the device and comprising data communication means laid out for transmitting the measured values to at least one communicating terminal comprising communication means laid out for receiving the values measured by the device and transmitting them to at least one centralization server, for which data processing means are laid out for calculating, from these values, parameters comprising at least one parameter relating to at least one slowdown in the rise of the values measured by the pressure sensors when the subject mounts the device.

According to another particularity, the data processing means of the centralization server are laid out for applying at least one of the calculation steps of the method according to the invention.

This object is also achieved by a system for assessing the balance of a subject, characterized in that it comprises a device for assessing the balance of a subject, including a plate intended for receiving the feet of a subject and mounted on a plurality of pressure sensors measuring vertical forces applied on the plate, and the data processing means dynamically collecting the values measured by the pressure sensors at least before and while the subject mounts the device and comprising data communication means laid out for transmitting the measured values to at least one communicating terminal comprising communication means laid out for receiving the values measured by the device and data processing means laid out for calculating from these values parameters comprising at least one parameter relating to at least one slowdown in the rise of the values measured by the pressure sensors when the subject mounts the device, the communication means of this communicating terminal also being laid out so as to transmit the measured values and/or the calculated parameters to at least one centralization server.

According to another particularity, the communicating terminal includes data processing means laid out for applying at least one of the calculation steps of the method according to the invention.

Figure 2:
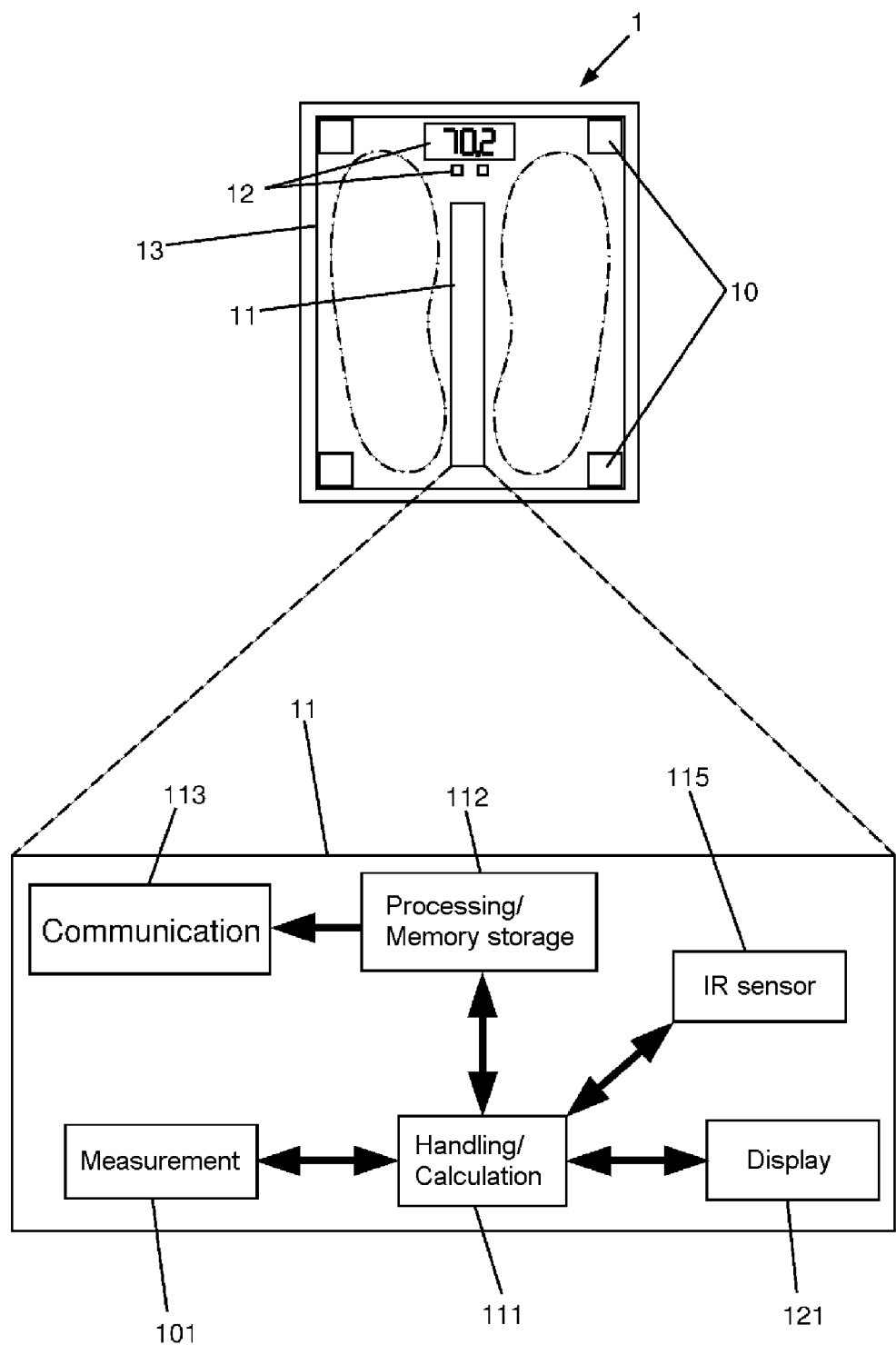
Figure 3A:
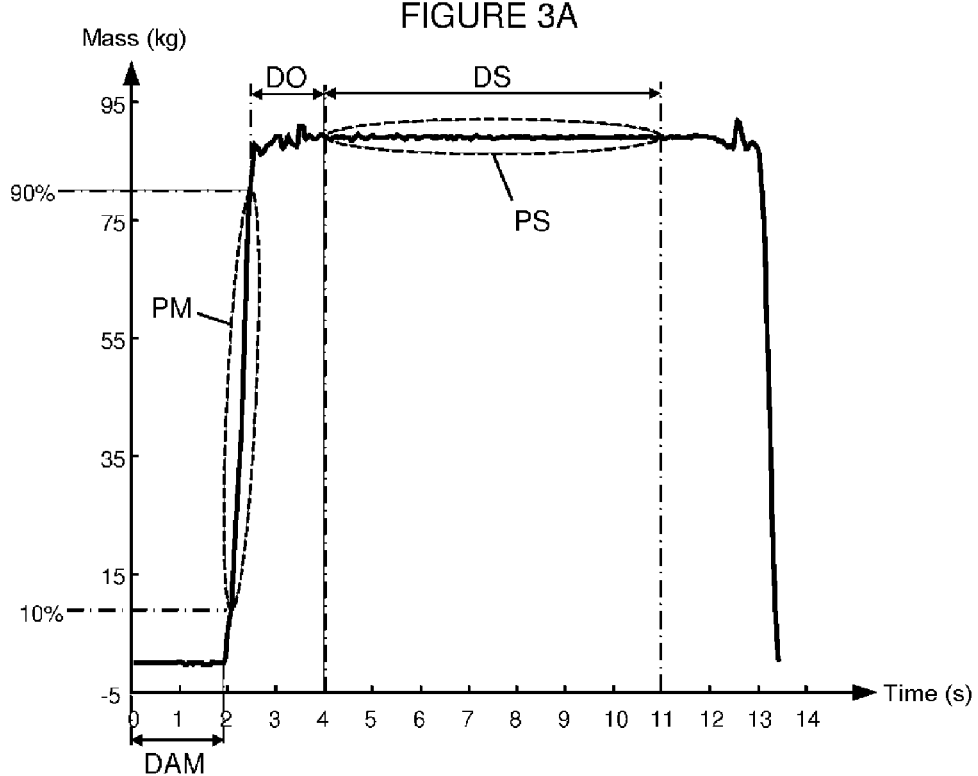
Figure 3B:
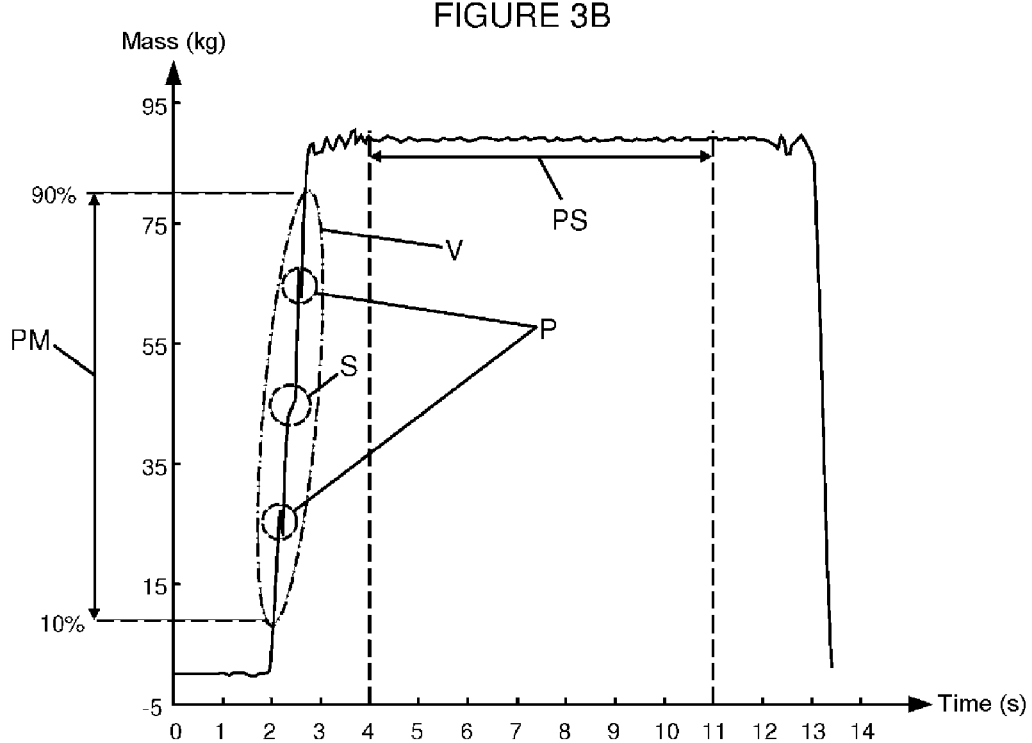
Figure 4:
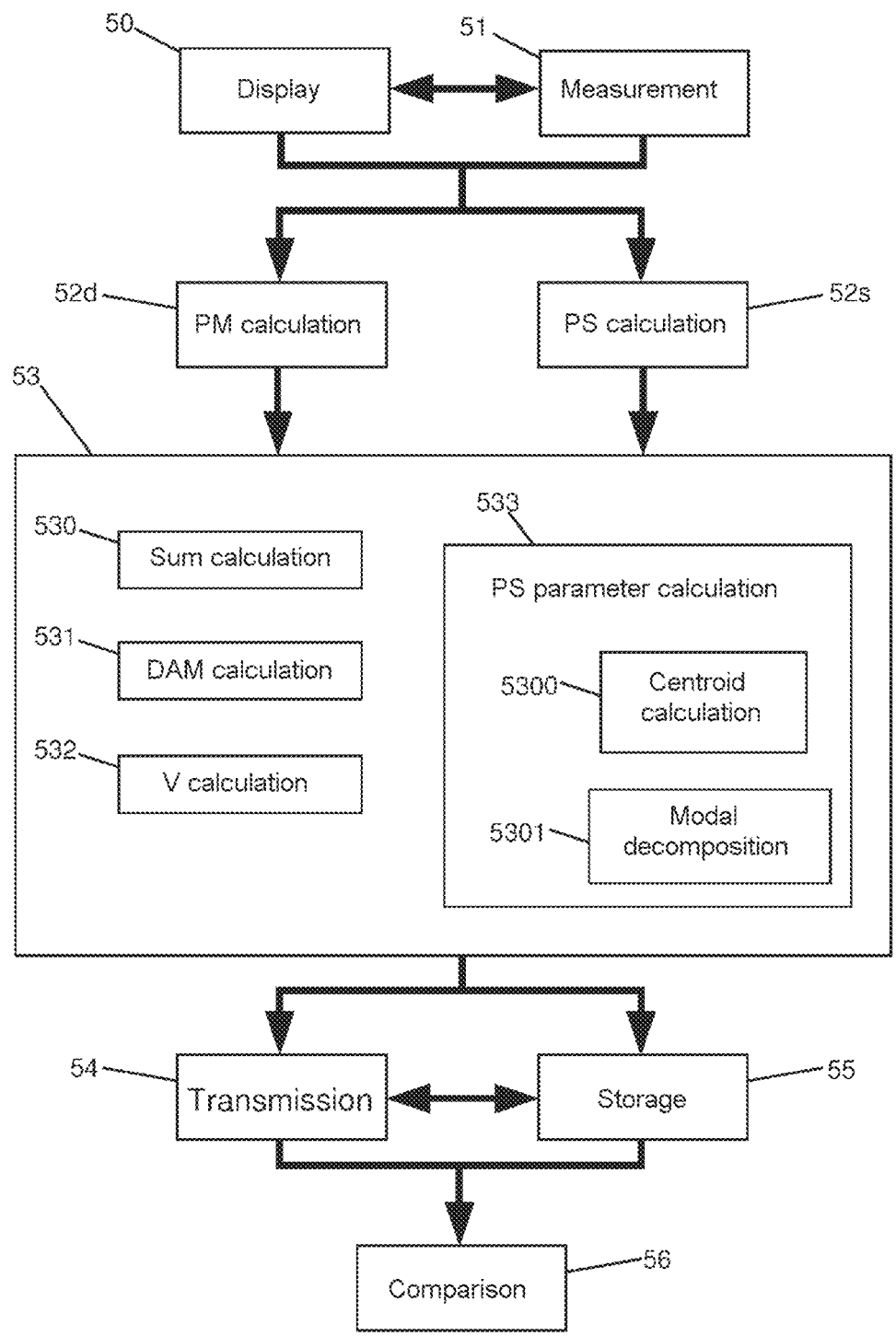
Figure 5:
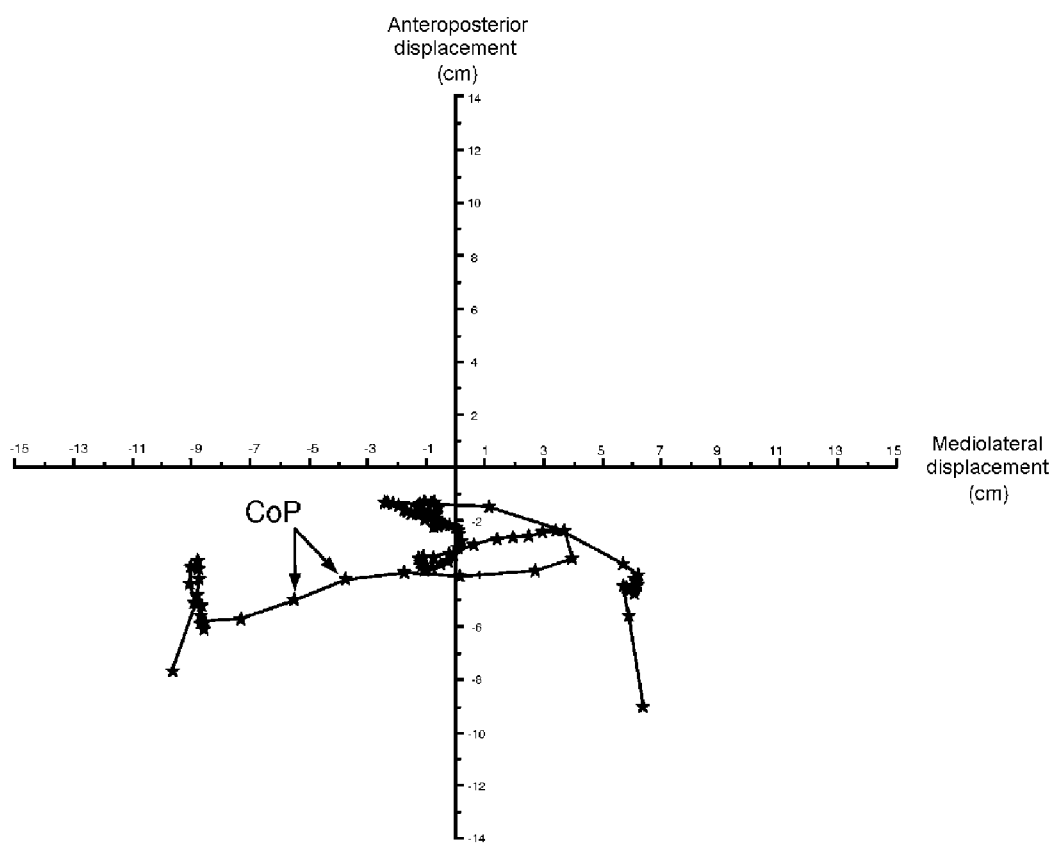
Figure 6:
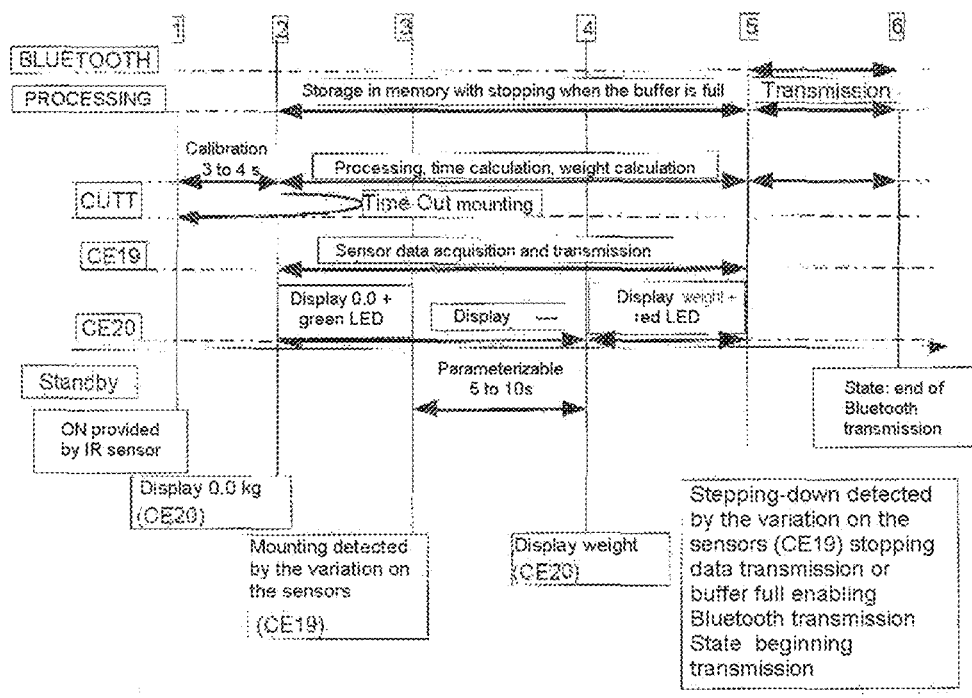

Other particularities and advantages of the present invention will become more clearly apparent upon reading the description hereafter, made with reference to the appended drawings, wherein:

FIG. 1 illustrates a system for assessing balance according to certain embodiments of the invention, FIG. 2 illustrates a device for assessing balance according to certain embodiments of the invention, with an example of implementation of the data processing means, FIGS. 3A and 3B show curves of values collected during an assessment according to certain embodiments of the invention, with various identified phases and various parameters to be calculated, FIG. 4 illustrates a method for assessing balance according to certain embodiments of the invention, FIG. 5 shows a stabilogram obtained by calculations according to certain embodiments of the invention, and FIG. 6 shows an illustrative and non-limiting example of the operations carried out during a measurement procedure.

The present invention relates to a method, a device and at least one system for assessing the quality of balance. Here, this will simply be referred to as assessment of balance.

The present invention proposes an original approach for non-invasive monitoring of the behaviour related to the risk of falling. Intuitively, the notion of balance naturally seems to be related to the risk of falling. The relevance of this assumption has already been verified in prior studies.

Most forecast studies are oriented towards the identification of major predictive factors in groups with a high risk of falling. The factors which most often return include muscular weakness, a previous fall, or balance and walking problems. Further, other factors mentioned as aggravating factors in terms of risk of falling, such as visual, vestibular or propioceptive problems, may be expressed by a problem of balance. In most of these studies, balance is assessed by using clinical and biomechanical tests. Although these tests have demonstrated their capability of identifying risks of falling within the year, they cannot identify gradual changes. Consequently, they are unsuitable for a daily test. Also, a simple biomechanical measurement of swaying and a few derived measurements like the area and the type of displacement of the pressure center have been able to predict falls. On the other hand, these measurements have never been integrated at home.

Further, there exist laboratory systems such as force platforms for studying stabilograms, but there does not exist any simple system for the home. It was therefore necessary to develop inexpensive tools for extracting the required information, preferably by the minimal disturbance of the usual life surroundings.

An originality of certain embodiments of the present invention is that they rely on a common object: scales. Indeed, certain embodiments of the invention are based on integrating into scales, means allowing assessment of the quality of balance. The device (1) for assessing balance is then scales which include a plate (13) intended for receiving the feet of a subject and mounted on a plurality of pressure sensors (10) measuring vertical forces applied on the plate (13), generally with display means (12) and modified for including data processing means (11) laid out for applying the method according to various embodiments of the invention. The sensors (10) will preferably be four in number, preferably distributed near the corners of the plate (13), as illustrated in FIG. 2, for proper measurement of the vertical forces (the weight exerted by the standing subject) and good stability of the plate of the device. Nevertheless, it is possible to increase or reduce the number of sensors (10) while preserving a reliable measurement (plates with only three sensors have already been successfully used). Such a simple device allows application of a simple procedure and with low risk for the subject, which the inventors have discovered that it may be sufficiently relevant for assessing the balance if it accompanied the detection of at least one event and the measurement of at least one parameter identified by the inventors, as detailed hereafter. This procedure simply requires that the subject mounts the measurement plate (13) of the device (1) in the same way as he/she generally does for weighing himself/herself.

The plate (13) preferably has dimensions adapted to the average size of the feet of the subjects, so as to get rid of problems related to the position of the feet of the subjects on the plate during measurements. For example, a substantially square plate with a size of about 30 cm or a rectangular plate allows the feet of the subjects to be always properly placed relatively to the sensors (10). Generally, the dimensions of one side of the plate (13) may be comprised between 15 and 70 cm, preferably of the order of 25 to 40 cm.

Further, the display means (12) of scales are generally positioned on the device (1) so that a subject standing on the plate (13) may see the display. The device (1) taking up again this arrangement in certain embodiments allows standardization of the posture of the subjects using the device (1). All the subjects stand, generally with their arms along the body, while looking at the display which is approximately located at their feet tips.

Finally, various embodiments of the invention are applied by inviting the person to mount the device. The device (generally scales) includes broadcasting means in order to provide the subject with information relating to an invitation to mount it. The scales for example display such an invitation (for example a green LED or on the display screen), the subject steps onto the plate, waits for his/her weight to be displayed, and then steps down from it (for example following the display of an invitation to step down, for example a red LED or an invitation on the display screen, or even simply the display of the weight of the subject which allows the latter to know that he/she may step down). Thus a simple procedure is obtained which does not change the habits of the subject, which may be particularly advantageous for certain particular subjects.

Thus, various embodiments of the invention are particularly adapted to their use at home since the subjects apparently have simply scales onto which they step, for example daily for measuring their weight, but which allows at the same time tracking of the quality of their balance. The invention of course allows tracking of several persons with a single device, by the handling of several profiles by means of data processing means (11) and of display means (12).

In certain embodiments, the device (1) set up at the home of the subject allows "continuous" tracking, first by training, and then by assessing the deviations relatively to the learned reference situation.

FIG. 1 illustrates a system for assessing balance according to various embodiments. The present invention may actually be applied on a single self-contained assessment device (1) or preferably be applied in a system comprising the assessment device (1) and at least one communicating terminal (2) and/or at least one centralization server (3). According to various embodiments, the data processing means (11) of this device (1) will therefore be laid out so as to carry out all or part of the steps of the method according to the invention. When the device does not carry out all the steps autonomously, it will then only be equipped with optional display means (12), with the plate (13) and with the sensors (10) and processing means (11) only laid out for collecting the data from the sensors, for controlling the optional display means (12), for collecting the values measured by the sensors (13) and for controlling the communication means (113) allowing transmission of the acquired data. In this case, the device (1) will be equipped with communication means (113) on at least one communications network (RC) for transmitting the data (measured values and/or calculated parameters) to at least one communicating terminal (2) and/or to at least one centralization server (3). The device (1) according to various alternatives, may then optionally perform or not at least one portion of the calculations for applying the method. This terminal (2) and/or this server (3) may carry out the steps of the method (notably the calculations) which will not have been carried out by the device (1). Alternatively, the means for transmitting (113) data of the device (1) may be replaced with removable storage means (such as for example a memory card reader for storing data). The thereby stored data may then be transmitted if necessary to a terminal (2) equipped with a reader for their processing. Nevertheless, the embodiments where the device (1) has communication means (113) for transmitting these data via a communications network (RC) are preferred for practical reasons.

Thus, in FIG. 1, several possible embodiments appear in fact:

Either the device (1) is laid out for directly transmitting its data to at least one communicating terminal (2) and/or at least one centralization server (3), for example by long distance communication means (for example an internet connection, via a local network or directing, or further through a telephone network, notably of the last generation), either wired or not, as illustrated by the rightmost arrow in FIG. 1 which directly extends from the device to the terminal (2) and/or the server (3). The communicating terminal (2) may for example be the computer of a physician who follows the time-dependent change of the balance of the subject (or of several subjects) and which thus regularly receives the data acquired by the assessment device(s) (1). The centralization server (3) may be a server of a service provider, which centralizes the data and their processing for a plurality of subjects and/or for a plurality of physicians following subjects for example.

Or the device (1) is laid out for transmitting its data to at least one communicating terminal (2), such as for example a mobile telephone or a computer, for example by short distance communication means (such as for example a Bluetooth connection, which is preferred here for its simplicity and relative universality, or a wired connection) or even long distance communication means (such as for example a wired or wi-fi connection), as illustrated by the top left arrow in FIG. 1. The communicating terminal (2) will in this case be the one of a subject who has access to the device (1) for tracking his/her balance. This terminal (2) of the subject is then laid out, either for directly transmitting the data (with here also as an alternative, the possibility of storage on a removable medium), transmitting the data to at least one communicating terminal (2) and/or to at least one centralization server (3), or for first processing the data by applying at least one portion of the steps of the method (notably the calculations detailed here) before transmitting them (or storing them in a removable medium). This second transmission of the terminal (2) of the subject to another terminal (2) or server (3) may then be accomplished for example by long distance communication means (for example an internet connection, via a local network or directly, or further through a telephone network, notably of the last generation), either wired or not, as illustrated by the bottom left arrow in FIG. 1. This second communicating terminal (2) which receives the data from the communicating terminal (2) of the subject may for example be the computer of a physician who follows the time-dependent change of the balance of the subject (or several subjects) and who thus regularly receives the data acquired by the assessment device(s) (1). The centralization server (3) may be a server of a service provider, which centralizes the data and their processing for a plurality of subjects and/or for a plurality of physicians following subjects for example.

It is therefore understood that the present invention is based on at least one device (1) for assessment of balance which allows at least measurements by means of a simple procedure and that the calculations which are then applied onto the acquired data may be performed locally on the device or at a distance on various types of terminal or server. The illustrative examples provided here are of course non-limiting and it will become apparent upon reading the present application that the invention may be applied by means of types of terminals other than those given here as an example, except for the assessment device (1) which will have to at least include the means described here (the processing means integrating all or part of the functions described here). Also, reference is made here to broadcasting means (12) which are preferably display means (12) for guiding the user but it will become apparent upon reading the present application that such means may assume various forms or be replaced with audio means or any other equivalent means allowing information to be delivered to the subject who uses the device (1), since the question is only to guide him/her in the measurement procedure which is very simple. For example, FIGS. 1 and 2 represent the display means (12) as a screen displaying information (for example the weight in kilograms) and LEDs (Light Emitting Diodes) for example indicating that the apparatus is in a standby or operating mode or waiting for the subject to step on it or step off it (according to various possible codes), but it will be understood that these are only illustrative examples and that either one of these means may be omitted or replaced with other means. Further, FIGS. 1 and 2 illustrate the processing means (11) as integrating means (112) for processing and storing data in memory. It will be understood that this may in fact be a buffer memory, for example of the volatile type only being used as a temporary storage for the transmission of data (or, in the aforementioned alternatives, the recording into a removable medium). The data processing means (11) are therefore laid out at least for applying the measurement procedure, with an invitation for mounting the plate, a possible invitation to wait, a possible display of the weight and a possible invitation to step down (each possibility may for example be replaced by the absence of any display or a neutral display). This application of the procedure requires control of the measurement with the sensors (10), control of the display, and control of the storage and memory and/or the transmission. FIG. 2 for example illustrates a handling/calculation module (111), which will control these means of the device (1), for example by means of a specific module (101, 121, 112, 113) for each means, as indicated in FIG. 2. On the other hand, the device (1) may be equipped with an infrared sensor detecting the presence of the subject and thus starting the procedure. A specific module (115) is illustrated for controlling such a sensor, but this module and this sensor may be omitted or replaced with other detection means. For example it is possible that it may be necessary to press on a button or on the plate in order to start the procedure. As mentioned earlier, the processing means (11), notably the handling/calculation module in the embodiments where it is present, is laid out for performing at least one portion of the steps of the method according to the invention. The steps required for the procedure will necessarily be handled by the processing means, but the calculations may be performed remotely on all or part on at least one communicating terminal (2) and/or on at least one centralization server (3).

The device (1) may, in certain embodiments, be laid out as illustrated in the example of FIG. 2. In this example, the data processing means (11) of the device (1) are illustrated according to a layout with different modules (111, 101, 121, 112, 113, 115) loaded with the different operations to be carried out. Nevertheless it will be understood that the invention may provide various types of layout, such as for example a single operational module accumulating the whole of the functions described here. These processing means (11) are electronic resources preferably directly integrated into the scales, such as for example electronic boards, but may in fact be associated with them, at least partly (for example by being remotely placed in another device communicating with the scales by means of the communication means). According to various embodiments, several different boards or a single circuit integrating all the functionalities may be provided. For example, a first board may be available which ensures the carrying out of the procedure and provides sensor data, and second board which allows the handling of the data sent by the first board, their temporary storage, and then their sending through a wireless interface to a reception system, whether this is a PC or a portable telephone.

As mentioned earlier, the invention i.a. relates to a method for assessing the balance of the subject, which is applied by means of at least one device (1) according to the invention. In certain embodiments, this method includes the following steps:
  Measuring (51) with the pressure sensors (10), vertical forces applied on the plate (13), at least while the subject mounts the device (1),
  Calculating (53), from these measured values, relevant parameters for the assessment.

In the preferred embodiments, the calculation step (53) allows the calculation of at least one parameter relating to at least one slowdown in the rise of the values measured by the pressure sensors (10) when the subject mounts the device (1). In certain embodiments, the method includes at least one broadcasting step, for example a display step (50), on broadcasting means, for example display means (12), for information relating to at least one invitation of the subject to step onto the device (1).

During the procedure which, as a reminder, only requires the subject to mount thereon, preferably following an invitation by the device (1), and then preferably maintaining the standing posture for a few seconds, the device (1) collects the values measured by the sensors (10), i.e. the vertical forces applied on each of the sensors (10) under the plate (13). FIGS. 3A and 3B show an example of the sum of the measurements of four sensors during a procedure where the subject steps up thereon, waits, and then steps off the device (1). The step (53) for calculating the relevant parameters for the assessment includes, for most embodiments, a step (530) for calculating the sum of the values measured by each of the pressure sensors (10). FIG. 3A does not show any slowdown in the rise, and FIG. 3B shows several types of possible slowdowns. Indeed, the curves measured for certain subjects do not have any slowdown. On the other hand, certain subjects, when they step onto scales, produce quite significant jolts because of a poor balance. This is expressed in the measurement by a peak in the rise, corresponding to a sudden slowdown. Other subjects have less significant imbalances which are expressed by a slight slowdown in the form of a sigmoid generally. Other subjects have both types of slowdowns (slight and sudden). Thus, the calculation (53) of the parameters relating to at least one slowdown may concern at least one sigmoid (S) and/or at least one peak (P) in the rise of the values measured by the pressure sensors (10), when the subject mounts the device (1). This is referred to as a slowdown in order to group together both notions of peaks and sigmoids, in order to simplify matters. Also, the term of sigmoid is not limiting and it should be understood as designating a slower and lower amplitude slowdown than the one designated as a peak. The parameters relating to these slowdowns may concern the presence and/or the specific characteristics of the slowdowns (peaks and/or sigmoids). As specific characteristics, it is for example possible to calculate the slowdown amplitude, its duration, etc. Indeed, the inventors of the present invention have discovered that even during such a simple procedure as the stepping of a subject onto a measurement plate, such as that of scales for example, the presence of a slowdown in the rise of the measured values was a particularly relevant parameter for assessing the balance of a subject. Thus, certain embodiments of the present invention are technical applications of this discovery. The method, the device and the system according to the invention then use at least one algorithm for detecting a slowdown in the rise of the values measured by the sensors. Further, this algorithm may be associated with or at least include one algorithm for calculating at least one parameter relating to this slowdown, such as for example those mentioned above. Thus, the invention preferably resorts to at least one calculation of at least one parameter relating to at least one slowdown in the rise of the values measured by the pressure sensors (10) when the subject mounts the device (1), this parameter being representative of the presence and/or of specific characteristics of the slowdown, as detailed above.

Generally, it is understood from the present application that algorithms implemented in the processing means (in the measuring device or in a terminal which is associated with it) may be provided for carrying out detections of events and of parameters relating to these events described in the present application (rising phase, delays before a rise, a slowdown, rising rate, stability phase, etc.).

In certain embodiments of the method, the step (53) for calculating the relevant parameters for the assessment is preceded with a step (52d) for calculating a rising phase (PM) of the values measured by the pressure sensors (10), when the subject mounts the device (1). FIG. 3A shows this rising phase (PM), with a substantially vertical ellipse with dotted lines (on the left, on the rising portion of the curve) and shows a so-called stability phase (PS) with a substantially horizontal ellipse in dotted lines (on the right, on the plateau portion of the curve).

The rising phase (PM) is, in certain embodiments, determined as the period during which the values measured by the sensors are located between 10% and 90% of a reference value reached once the subject has mounted the device (1). This reference value may correspond to the calculated weight of the subject, taken on the plate (maximum value) from the values measured by the sensors. During the calculation of the reference value, certain embodiments preferably provide filtering of rapid signals such as short oscillations at the end of the rise, in order to get rid of errors due to local maxima. For example, according to various alternatives, this maximum value will be calculated on a strongly smoothed curve (for example by means of an average calculated on a sliding window) or will be calculated by an average over several seconds, at a sufficiently long delay after the beginning of the rise. Other methods for obtaining a reliable reference value are possible and within the reach of the person skilled in the art. At least one portion of said calculated parameters corresponds to values calculated during this rising phase (PM). In certain embodiments of the method, the step (53) for calculating relevant parameters for the assessment is preceded with a step (52s) for calculating a so-called stability phase (PS), of values measured by the pressure sensors (10), when the subject mounts the device (1). This is referred to as a stability phase since the pressure values measured by the sensors increase when the subject mounts the device and stabilize at a plateau value. This stability is relative since, the values continue to oscillate depending on the quality of the balance of the patient, which moreover allows calculation of a stabilogram and various relevant parameters as detailed in the present application. In certain embodiments, this stability phase (PS) is determined as the period starting at a determined delay (DO), a so-called waiting delay, after said measured values have attained 90% of the reference value and ending at a determined delay (DS), a so-called stability delay, after said waiting delay (DO). In certain embodiments, the step (53) for calculating the relevant parameters for the assessment may include at least one step (533) for calculating parameters relating to this stability phase (PS). The waiting delay (DO) is of the order of 1 second (comprised between 0.5 and 2 seconds, for example 1.5 seconds) and the stability delay (DS) is of the order of 5 to 10 seconds (comprised between 3 and 20 seconds). FIG. 3B again shows these two phases (PS, PM) by indicating with a vertical arrow the amplitude (10 to 90%) assumed for the rising phase (PM) and the time interval taken (4 to 11 seconds) for the stability phase (PS). It is therefore understood that the calculations involve parameterized values such as the waiting (DO) and stability (DS) delay and measured values (such as the reference value for example the maximum in the plateau of the curve, in order to calculate 10% and 90% thereof).

As regards the rising phase (PM), in certain embodiments, the step (53) for calculating the relevant parameters for the assessment includes a step (532) for calculating at least one parameter relating to the rising rate (V) of the values measured by pressure sensors (10) when the subject mounts the device (1). FIG. 3B shows with an ellipse in dotted lines the portion of the curve on which this rate (V) will be calculated, i.e. the whole rising phase (PM) in this example. In certain embodiments, the step (53) for calculating the relevant parameters for the assessment includes a step (531) for calculating at least one parameter relating to the elapsed delay (DAM) between the invitation to step up thereon and the stepping of the subject onto the device (1).

As regards the stability phase, the step (53) for calculating the relevant parameters for the assessment, as for example the step (533) for calculating parameters relating to the stability phase (PS), includes a step (5300) for calculating the centroid of the vertical forces measured by each of the pressure sensors (10) in order to determine the position of the pressure center (CoP, FIG. 5) corresponding to the projection of the center of gravity of the subject onto the plate (13). This position of the pressure center (CoP) over time, during the stability phase (PS) provides a stabilogram, an example of which is illustrated in FIG. 5. Such a stabilogram allows application of a modal decomposition step (5301) in order to extract intrinsic modal functions therefrom. The parameters relating to the stability phase (PS) which may be used in the present invention, may for example include at least one parameter determined on these intrinsic modal functions. For example, the representation of these intrinsic modal functions in a so-called phase space, may assume the form of ellipses, for which the length (i.e. the largest dimension) and the width (the smallest dimension) are calculated. This example of the ellipse dimensions should not be interpreted in a limiting way although this parameter has been determined as being particularly useful and the invention covers various types of parameters calculated on a modal decomposition of the signal. Thus, certain embodiments may use one or several calculation algorithms for representation in phase space and the calculation of parameters relating to the obtained ellipses, notably for example the length and/or the width (which are relevant and the calculation of which advantageously requires not many resources).

In certain embodiments, it is possible to only focus on the rising phase (PM) (dynamic phase). A method (and a device and a system) is thereby obtained in which for example at least the parameters relating to this rising phase (PM), such as for example slowdowns (peaks and/or sigmoids) are calculated. It is also possible to envision a method in which at least the parameters relating to the delay before the rise (DAM) and/or to the rising rate (V) described hereinbefore, are calculated. Indeed, the inventors of the present invention have discovered that even during such a simple procedure as the stepping of the subject onto a measuring plate, such as that of scales for example, the delay before stepping thereon (DAM) or the rates (V) for stepping thereon were relevant parameters for assessing the balance of the subject. Thus, certain embodiments of the present invention are technical applications of this discovery by the use of algorithms relating to at least one of these parameters.

In other embodiments, it is possible to only focus on the static phase (PS). A method (and a device and a system) is thereby obtained in which for example at least the parameters relating to the static phase (PS) are calculated, such as for example the modal decompositions of the stabilograms described hereinbefore. For example a method for assessing the balance of a subject is thereby obtained, characterized in that it is applied by means of at least one device including a plate (13) intended for receiving the feet of a subject and mounted on a plurality of pressure sensors (10) measuring vertical forces applied on the plate (13). The method may then include the following steps:

Measuring (51), with the pressure sensors (10), vertical forces applied on the plate (13) during the presence of the subject on the device (1), Calculating (53) from these measured values, relevant parameters for the assessment, comprising at least one step (52$s$) for calculating a so-called stability phase (PS), of the values measured by the pressure sensors (10) when the subject mounts the device (1), this stability phase (PS) being determined as the period starting after at least one determined delay after the invitation to mount the device, and then at least one step (533) for calculating parameters relating to this stability phase (PS) including a step (5300) for calculating the centroid of the vertical forces measured by each of the pressure sensors (10) in order to determine the position of the center of pressure (CoP) corresponding to the projection of the centre of gravity of the subject onto the plate (13) and providing a stabilogram allowing application of a modal decomposition step (5301) for extracting intrinsic modal functions therefrom, the parameters relating to this stability phase (PS) comprising at least one parameter determined on these intrinsic modal functions.

However, in the preferred embodiments, calculations on the static phase (PS) and those on the rising phase (PM) will be combined since studies have shown that both of these aspects should be taken into account for assessing the balance in a way as most relevant as possible. Thus, the preferred approach merges complementary pieces of information related to the quality of static balance and to the quality of dynamic balance, and the parameters provided here are particularly efficient for assessing balance.

It will be noted that it is preferred here that reference be made in the present application to an invitation of the subject to mount the device and that this invitation gives the possibility of calculating the delay before the mounting (DAM) of the subject, since it provides a reference time. In embodiments where this calculation of the delay (DAM) will be omitted, this invitation may also be omitted. Thus, in certain embodiments, the invention does without this characteristic. Generally, the various steps and/or characteristics provided in the present application, notably with reference to a particular embodiment, may be isolated from the other steps and/or characteristics or combined with other steps and/or characteristics, unless the opposite is explicitly mentioned or it appears that isolation or combination is impossible or results in a solution which does not operate.

On the other hand, reference is mainly made here to this invitation to step up thereon and to the calculations made from these measurements on the rising phase. Nevertheless the person skilled in the art will understand upon reading the present application that is also possible to perform calculations on the stepping-off phase (when the subject steps off the device). For example, waiting delays and reference value percentages like for the rising phase may also be determined in order to determine a period defining the stepping-off phase. The parameters calculated on such a stepping-off phase may for example be equivalent to those of the stepping-on phase, such as a delay before stepping off (an elapsed delay between an invitation to step off and the stepping-off of the subject), a stepping-off rate (decreasing slope of the measured values), the presence (and/or characteristics) of slowdowns (peaks and/or sigmoids) in the stepping-off, etc. Other parameters may also be calculated on this stepping-off phase. Indeed, the inventors have observed such events during stepping-offs and have discovered that they were relevant, even in the case of stepping off a plate such as the one of scales, which is generally less high than the obstacles used in clinical assessments and which is consequently adapted to home use having less risk for subjects for which risks of falling are high.

FIG. 4 schematically illustrates an exemplary method according to various embodiments of the invention. All the steps are illustrated therein, but it will be understood from the present description that some of them may be omitted. Also, it will have been understood from the foregoing that all these steps are not necessarily applied in a single and same device (notably as regards the calculations which may be performed remotely as detailed hereinbefore).

Thus, some embodiments of the method include at least one step (54) for transmitting the measured values and/or the calculated parameters, through communication means (113) of the device (1), to at least one communicating terminal (2) and/or at least one centralization server (3), via at least one communications network (RC). Also, certain embodiments (not excluding the previous ones), include at least one step (55) for storing the measured values and/or the calculated parameters in memory storage means (112, 212, 312).

Preferably, the method includes at least one calculation step (56) for comparing the measured values and/or the calculated parameters, stored in the memory storage means (112, 212, 312), for at least two determined assessments of a same subject, in order to allow tracking of the time-dependent change in the quality of the balance. Thus, regardless of whether the data are stored in memory storage means (112) of the device (1), in memory storage means (212) of a communicating terminal (2) or in memory storage means (312) of a centralization server (3), the method may allow a comparison of the performances of a subject relatively to his/her previous performances. A method allowing detection of degradations of balance is thereby obtained. The invention moreover provides automated processing allowing automatic alerts (on at least one of the devices of the system). In certain embodiments, the analysis of the collected parameters may require the intervention of a skilled operator (for example, a specialist of the invention and/or a physician trained for its use), for example on a terminal (2). It will be noted that examples of a mobile telephone and of a computer for the terminal (2) have only been given but the invention may be implemented in other devices having sufficient electronic resources.

It will be noted that the present invention performs calculations from simple pressure measurements. This has been made possible by validation of the method, notably as regards the center of pressure (CoP). Indeed, the centers of pressure are not calculated in the same way starting with a force platform and scales. The data of a force platform are expressed in moments and forces for the three axes x, y and z (Mx, My, Mz, Fx, Fy, Fz). The pressure center is calculated from the moments and forces according to the formulae below:

$$AP = \frac{M_y}{F_z}, ML = \frac{-M_x}{F_z}$$

The vertical force of the force platform is directly available without calculating (Fz).

Not having any data on the moments for scales, the method used is fundamentally different. The trajectory of the pressure center is determined by calculating the centroid of the vertical forces measured by the four sensors of these scales.

This method had to be validated by putting the device (1) in the center of a force platform integrated into the ground, by compensating the force exerted by the device (1) on the platform by means of a Wheatstone bridge of this platform and by comparing the measurements with the two techniques and with various experimental measurements. This study allowed validation of the method, of the device (1) and of the assessment system, presented in the present application.

Possible implementation details are provided hereafter, in a perfectly illustrative and non-limiting way with reference to the embodiments where the device (1) includes data processing means for applying all the functionalities described in the present application (with a board for each function). This list details the various means with their function:

The infrared sensor awakens the handling/calculation board as soon as it detects a presence, it uses a polling operation for limiting consumption.

The handling/memory storage board performs the operations:
  Storing the received data in memory, and then sending the memory stored data to the Bluetooth board via a specific link (for example RS232).
  The beginning of the memory storage begins with detection of the data sent by the handling/calculation board (presence of a frame).
  Memory storage stops as soon as there is no longer any frame or else when the memory is full.
  As soon as the memory storage stops, the data containing the memory are transmitted over the specific link to be sent via Bluetooth.
  The maximum size of the data corresponds to about 15 s of measurement, i.e. about 4 kb. If the buffer is full, one switches to Bluetooth transmission.

The handling/calculation board performs the operations:
controls the processing/memory storage, measurement and display boards, handles the measurement time when the person is on the scales, as well as the following timeout:
  The infrared sensor awakens the handling/calculation board, nothing else occurs afterwards, there is no detection of mounting (the person appears without stepping up, or else the sensor is triggered without the presence of the person), and returns to the standby mode.
  If there is a calibration error (between phases 1 and 2) then one returns to the standby mode.
Handling the power supply of the processing/memory storage, measurement and display boards.
With the measurement board, it carries out calibration, sends the initialization frame to the processing/memory storage board.
  It displays 0.0 and orders the switching on of the green LED in order to indicate that the person may step thereon.
  It recovers the measurements of the measurement board, calculates the time and sends these data to the handling/memory storage board.
  It detects the fact that the person has stepped up thereon, it sends the display of "- - -" to the display card, and begins timing of the measurement time comprised between 5 and 10 s, during this time, it always sends the data from the sensors and the time to the handling/memory storage board.

At the end of the measurement time, it calculates the weight, sends the weight to the display card and orders the switching on of the red LED so as to tell the person that he/she may step down.

It continues to send the values of the sensors and the time to the handling/memory storage board.

It detects the fact that the person has stepped down, stops the sending of the sensor data, sends the weight to the handling/memory storage board.

It waits for the signal for the end of the Bluetooth emission so as to stop powering the measurement, display and processing boards.

If the person steps down before the red LED is switched on, the weight will not be displayed and the handling/calculation board will send an error code in the weight frame.

The sampling frequency of the measurement board is 16 Hz.

The display board integrates the red and green LEDs.

The scales are powered with a battery. When the charge of the battery becomes too low, the red and green LEDs blink instead of being permanently switched on during the authorization for stepping up and stepping down, a low battery message is then sent via Bluetooth, when data are sent.

There exist 3 types of data frames between the handling/calculation board and the processing/memory storage board:
An initialization frame (beginning of transmission): calibration data of the sensors,
Sensor data frame: values of 4 sensors, time interval between two measurements;
Weight frame (end of transmission): byte, error, weight.

Details of the procedure and of the display steps for guiding the subject are provided hereafter, in a perfectly illustrative and non-limiting way:

The weighing cycle begins as soon as the person is positioned in front of the scales. The infrared sensor detects the laying of the first right foot of the person and begins the phase for initializing the scales. Horizontal lines are displayed on the dial and tell the person that he/she has to wait.

When "0.0" is displayed and when the green LED is switched on, acquisition of the data from the sensors begins. The person should then step onto the scales. If the scales do not detect any weight after 15 s, the cycle is interrupted. As soon as the scales detect a minimum force of 5 N, it again displays horizontal lines on the dial and the green LED is switched off.

After waiting for 10 seconds, the scales display the weight of the person on the dial and the red LED is switched on. The person may then step down. Acquisition of the data from the sensors is stopped when the force exerted on the scales is below 5 N. The red LED is switched off and the dial again displays horizontal lines.

The data remains stored for ten minutes in the memory of the second board. If they are not transferred within the time limit, the scales switch off and the data are then lost.

Details of the implementation of the data transfer and of their subsequent handling or use are provided hereafter, in a perfectly illustrative and non-limiting way:

The data of the scales are transferred via a Bluetooth link. According to the site for collecting data, the latter are recorded locally, for example either on a PC (case of the centers for which several persons will be tracked by the same system) or in a portable telephone. The transfer software package is a proprietary application. The data are received and then transferred to a server by means of a web service.

The data are then listed in a data base according to the identifiers of the assessment site and of the subject. These sensor data are automatically used in order to calculate the vertical resulting force and the coordinates of the trajectory of the pressure center.

These three types of data are then available on an internet site, for which access may be protected by a login name and a password. Once connected, the user has access to all the recorded files which he/she is authorized to consult.

The selection of files may be accomplished by using a selection panel which allows selection of the files according to the measurement site (private home, EHPAD, etc.) of the subject, or by the file type (data of the scales, clinical data, etc.).

Once the data are selected, it is possible to download them.

As regards the scales, there may exist three types of files, for example with the CSV (Comma-Separated Values) format for facilitated compatibility:
BDPP files which contain the raw data of the four sensors of the scales,
BVP files which contain the values of the resulting force on the axis z,
BCPMM files which contain the coordinates of the trajectory of the pressure center calculated with the centroid method.

The data are then transferred to a PC which allows display of the results of a weighing operation.

It is understood that the present invention is particularly suitable for tracking the time-dependent change in the balance of a given individual. However, by accumulating data relating to the balance of the individuals, it is possible to form a normative data base allowing the use of the invention in a one-time assessment of the balance of an individual.

The invention may be used as a scientific non-invasive tool for quantitatively characterizing the performance of the postural control system of humans. The technique used here has many scientific, research and practical applications. For example, a normative data base may be established, and from this data base, comparisons may be made. These comparisons may be used for assessing the changes in the postural stability level resulting from injuries, a disease or from the aging process.

On the other hand, the technique may be used in rehabilitation procedures. For example, if the subject has developed a disease or was injured, the recovery rate may be tracked by monitoring balance by means of the invention.

Further, the technique may be used as a basis for biofeedback and methodology techniques aiming at improving the balance and the stability of the individual.

Moreover the invention may be used by designers of prostheses for measuring the influence of prostheses on postural stability.

Further, it is contemplated that the invention may be used for assessing the effect which various drugs have on the balance of an individual. For example, a control group may have received a placebo and a study group may have received a particular drug to be studied. An analysis of balance would be carried out in order to compare both groups and determine a possible effect of the drug on the study group.

Finally, the invention may be used by neurology departments of hospital, of ministries and geriatric programs, homes for the elderly and communities, hospitals for preventive care and medical centers, rehabilitation hospitals, international space programs, industries in which workers have risks of falling, insurance companies, biomedical research, engineering and teaching programs, research in physical therapy and teaching programs, medical schools, state schools and local police services (for example, sobriety control points), sports programs, physical exercise conditioning centers and sports shoes corporations.

FIG. 6 shows an illustrative and non-limiting example of the operations carried out during a measurement procedure (in the example with Bluetooth and with the boards described in the provided example on the implementation details above). In FIG. 6, the measurement board is designated with reference CE19, the display board is designated with reference CE20 and the handling/calculation board is designated with the reference CUTT.

It should be obvious that for persons skilled in the art that the present invention allows embodiments in many other specific forms without departing from the field of application of the invention as claimed. Therefore, the present embodiments should be considered as an illustration, but may be modified in the domain defined by the scope of the appended claims, and the invention should not be limited to the details given above.

The invention claimed is:

1. A method for detecting an impairment of balance of a subject, with at least one device including a plate mounted on a plurality of pressure sensors, the method comprising:
    measuring, with the pressure sensors, vertical forces applied on the plate at least when the subject mounts the device,
    assessing the balance, by calculating a rise rate of a sum of the vertical forces measured by the pressure sensors when the subject mounts the device,
    detecting the impairment of balance, by calculating one or more parameters, comprising at least one parameter in relation to at least one slowdown in the rise rate of the sum of the vertical forces measured by the pressure sensors when the subject mounts the device, the at least one slowdown being defined by at least one of a peak, a sigmoid, or a reduction in the rise rate, and
    alerting the subject of the detected impairment of balance.

2. The method according to claim 1, further comprising visual or audio signaling, for information relative to at least one invitation of the subject to mount the device,
    wherein said calculating one or more parameters includes calculating at least one parameter relating to an elapsed delay between the invitation to mount and the subject mounting the device.

3. The method according to claim 1, wherein said calculating one or more parameters is preceded with calculating a rising phase of the vertical forces measured by the pressure sensors, when the subject mounts the device, the rising phase being determined as a period during which said vertical forces are located between 10% and 90% of a reference value of vertical forces attained once the subject has mounted the device, at least one portion of said one or more parameters corresponding to values calculated from the rising phase.

4. The method according to claim 1, wherein said calculating one or more parameters is preceded with calculating a so-called stability phase, of the vertical forces measured by the pressure sensors, when the subject has mounted the device, the stability phase being determined as a period starting at a determined delay, a so-called waiting delay, after said measured vertical forces have attained 90% of a reference value and ending with a determined, so-called stability delay, after said waiting delay, said calculating said one or more parameters comprising at least calculating parameters relating to the stability phase.

5. The method according to claim 4, wherein the calculating parameters relating to the stability phase includes calculating a centroid of the vertical forces measured by each of the pressure sensors for determining a position of a pressure center corresponding to a projection of a center of gravity of the subject onto the plate.

6. The method according to claim 5, wherein said determining the position of the pressure center, during the stability phase, provides a stabilogram allowing an application of a modal decomposition step for extracting therefrom intrinsic modal functions, the parameters relating to the stability phase comprising at least one parameter determined from the intrinsic modal functions.

7. The method according to claim 1, further comprising transmitting the measured vertical forces and/or said one or more parameters, through a communication connection of the device, to at least one communicating terminal and/or to at least one centralization server, via at least one communications network.

8. The method according to claim 1, further comprising storing the measured vertical forces and/or said one or more parameters in memory storage.

9. The method according to claim 8, further comprising calculation for comparing the measured vertical forces and/or said one or more parameters, stored in the memory storage, for at least two determined assessments of a same subject, in order to allow tracking of a time-dependent change in a quality of the balance.

10. A device for detecting an impairment of balance of a subject, the device comprising:
    a plate configured for receiving feet of the subject and mounted on a plurality of pressure sensors for measuring vertical forces applied on the plate, and
    a data processor configured for:
        assessing the balance, by calculating a rise rate of a sum of the vertical forces measured by the pressure sensors when the subject mounts the device,
        detecting the impairment of balance, by calculating one or more parameters, comprising at least one parameter in relation to at least one slowdown in the rise rate of the sum of the vertical forces measured by the pressure sensors when the subject mounts the device, the at least one slowdown being defined by at least one of a peak, a sigmoid, or a reduction in the rise rate, and
        alerting the subject of the detected impairment of balance.

11. The device according to claim 10, wherein the plate has dimensions adapted to an average size of feet of one or more additional subjects.

12. The device according to claim 10, further comprising a visual or audio signal emitter that includes a display positioned on the device for the subject standing on the plate to see the display, so that a posture of the subject using the device is standardized.

13. The device according to claim 10, further comprising memory storage for storing the measured vertical forces and/or said one or more parameters.

14. A system for detecting an impairment of balance of a subject, said system comprising
    at least one device according to claim 10, the at least one device including a communication connection, and at least one centralization server and at least one communicating terminal comprising a communication connection configured to receive the measured vertical forces and/or said one or more parameters through the communication connection of the at least one device and transmit the measured vertical forces and/or said one or more parameters to the centralization server.

15. A system for detecting an impairment of a balance of a subject, said system comprising a device comprising a plate configured for receiving feet of the subject and mounted on a plurality of pressure sensors measuring vertical forces applied on the plate and a data processor dynamically collecting the vertical forces measured by the pressure sensors at least before and while the subject mounts the device and comprising a data communication connection laid out for transmitting the vertical forces measured to at least one communicating terminal comprising a communication connection laid out for receiving the vertical forces measured by the pressure sensors and transmitting them to at least one centralization server, wherein the data processor is configured for:

assessing the balance, by calculating a rise rate of a sum of the vertical forces measured by the pressure sensors when the subject mounts the device, detecting the impairment of balance, by calculating one or more parameters, comprising at least one parameter in relation to at least one slowdown in said rise rate of the sum of the vertical forces measured by the pressure sensors when the subject mounts the device, the at least one slowdown being defined by at least one of a peak, a sigmoid, or a reduction in the rise rate, and alerting the subject of the detected impairment of balance.

16. A system for detecting an impairment of balance of a subject, said system comprising a device for assessing the balance of the subject, including a plate configured for receiving feet of the subject and mounted on a plurality of pressure sensors measuring vertical forces applied on the plate, and a data processor dynamically collecting the vertical forces measured by the pressure sensors at least before and while the subject mounts the device and comprising a data communication connection laid out for transmitting the vertical forces measured to at least one communicating terminal comprising a communication connection laid out for receiving the vertical forces measured by the pressure sensors, wherein the data processor is configured for:

assessing the balance, by calculating a rise rate of a sum of the vertical forces measured by the pressure sensors when the subject mounts the device, detecting the impairment of balance, by calculating one or more parameters, comprising at least one parameter in relation to at least one slowdown in the rise rate of the sum of the vertical forces measured by the pressure sensors when the subject mounts the device, the at least one slowdown being defined by at least one of a peak, a sigmoid, or a reduction in the rise rate, and alerting the subject of the detected impairment of balance.

17. The system according to claim 16, wherein the communication connection of the communicating terminal is also configured to transmit the vertical forces measured and/or said one or more parameters to at least one centralization server.

* * * * *